United States Patent [19]

Wertheim et al.

[11] Patent Number: 5,148,041

[45] Date of Patent: Sep. 15, 1992

[54] REFLECTOMETER

[75] Inventors: Herbert Wertheim, Coral Gables; Hernan Bormey; Carlos Bormey, both of Miami, all of Fla.

[73] Assignee: Brain Power, Inc., Miama, Fla.

[21] Appl. No.: 652,016

[22] Filed: Feb. 7, 1991

[51] Int. Cl.⁵ .............................................. G01B 9/00
[52] U.S. Cl. .................................................. 250/571
[58] Field of Search .............. 250/571, 227.15, 358.1, 250/359.1; 356/445

[56] References Cited

U.S. PATENT DOCUMENTS

| | | | |
|---|---|---|---|
| 2,451,501 | 10/1948 | Liben | 88/14 |
| 3,690,774 | 9/1972 | Kottle et al. | 250/571 |
| 4,054,391 | 10/1977 | Witte | 356/209 |
| 4,284,356 | 8/1981 | Heilman | 356/429 |
| 4,364,663 | 12/1982 | Gardner et al. | 356/371 |
| 4,479,714 | 10/1984 | Lehrer | 356/445 |
| 4,591,271 | 5/1986 | Byers | 356/432 |
| 4,673,818 | 6/1987 | Guerra | 250/571 |
| 4,785,336 | 11/1988 | McComb et al. | 356/382 |

Primary Examiner—Janice A. Howell
Assistant Examiner—Richard Hanig
Attorney, Agent, or Firm—Luedeka, Hodges, Neely & Graham

[57] ABSTRACT

A reflection meter for measuring the percentage of reflected light from a surface. A light source produces light which strikes the surface. The surface reflects the light into a chamber which directs the light to a detector. The detector senses the reflected light and produces a detect signal that represents the light reflected. A microprocessor receives the detect signal and calculates a percentage of light reflected from the surface which is shown on a display. An absorbing receiver engage the surface and absorbs any light that is transmitted through the surface.

12 Claims, 3 Drawing Sheets

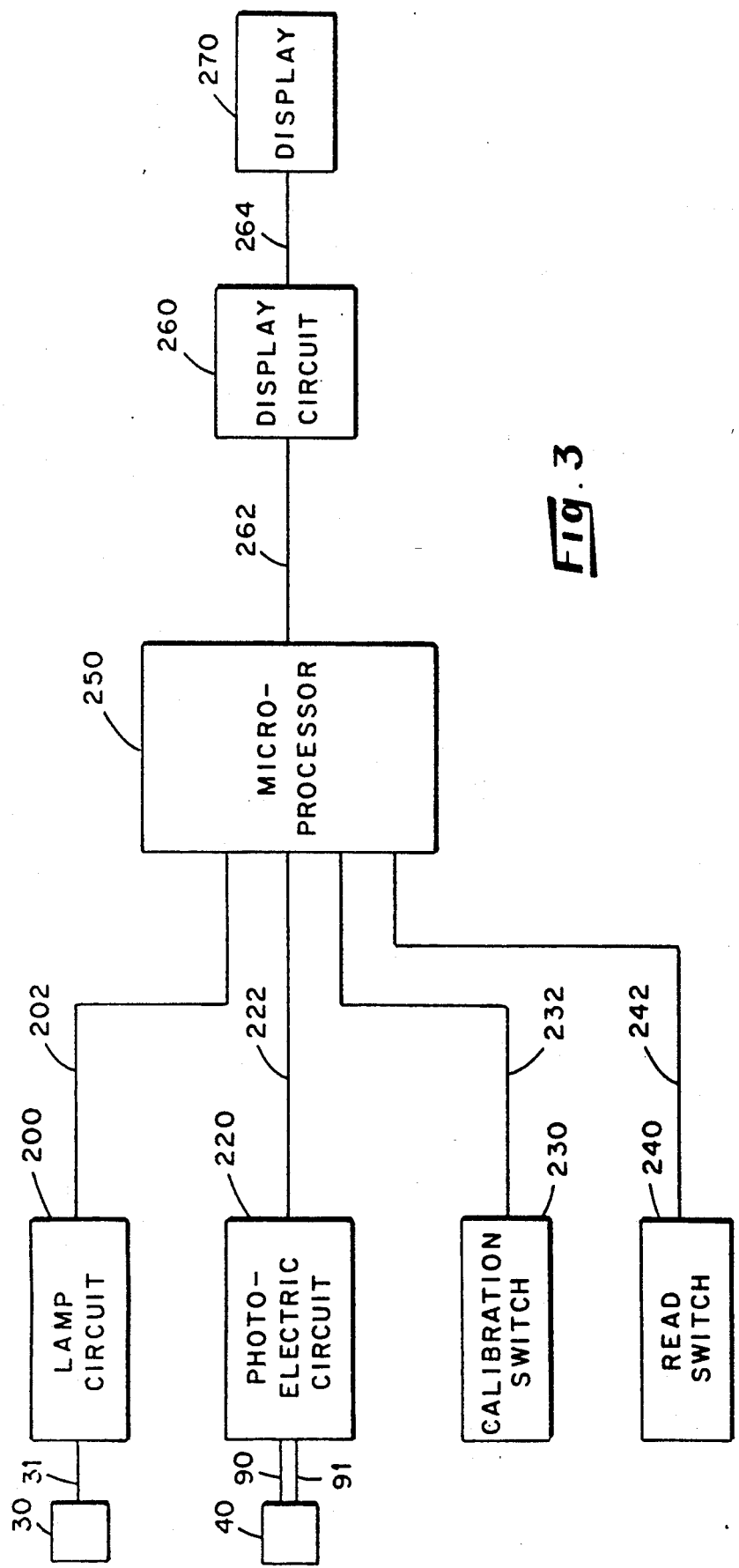

a
REFLECTOMETER

BACKGROUND OF THE INVENTION

The present invention relates to the measuring the reflectance of light from a surface, and more specifically the light reflected from an eyeglass lens. Furthermore, the present invention measures the reflectance of a surface in percentage reflection.

It is often useful to measure the reflectance of light from a surface. For example, when coating lenses with anti-reflective materials, the reflectance of a surface needs to be checked to verify that the lens has the proper reflectance characteristics. Several devices have been designed to measure lens reflection and optical density. For example, the Liben U.S. Pat. No. 2,451,501 discloses a specular reflectometer that measures the reflectance of flat and curved surfaces used in searchlights and the like. The Liben devices uses a semi-transparent mirror mounted inside a housing. The light source then transmits the light through a lens and the semi-transparent mirror onto the surface. The light reflects from the surface back to the semi-transparent mirror and onto a photoelectric cell. The transmission of light through the lens and the semi-transparent mirror, and the reflecting of light from the surface and the semi-transparent mirror, will cause the light to be repetitively diffused and absorbed. This diffusion and absorption is a disadvantage of the Liben system.

The Heilman U.S. Pat. No. 4,284,356 discloses a method of comparing the reflectance of opposing surfaces. The Heilman device uses light beams directed to opposing sides of a surface. The reflection of these beams are sensed and compared to determine which side of the surface has a reflective coating.

The known reflectance meters are generally bulky and complicated compared to the present invention. The present invention provides a meter that is easy to use and accurate, and, in fact, it is difficult to obtain inaccurate data with this device. In addition, the unique construction of the present invention provides a compact instrument that is relatively simple to manufacture, requires no elaborate optical alignment, and is easy to calibrate. Because of its compact size and easy operating procedures, the present invention is ideal for use in eye health care facilities by both skilled doctors and eye care assistants.

SUMMARY OF THE INVENTION

The present invention relates to a reflectometer or a reflection meter for measuring the reflectance of light from a surface, such as a lens. It includes a light source, chamber, a detector and a display means. The light source produces light that is directed toward the surface, and the chamber isolates, at least partially, stray light from the light source and the reflected light. The chamber has a window formed in it that is used for transmitting the light from the light source to the surface.

The detector detects the light reflected from the surface and produces a detect signal corresponding to the intensity of the reflected light. The detector is positioned out of the path of the light produced by the light source and in the path of the light reflected from the surface.

In the preferred embodiment, a fiber optic cable (or other light guide) receives the light from the light source and directs the light toward the surface and away from the detector, preferably a photoelectric detector. The detector has a hole located in the center for the fiber optic cable, and the fiber optic cable is disposed through the hole of the detector. In this construction, the fiber optic cable directs light away from the detector and allows the reflected light to directly strike the detector. This provides an accurate means to measure light reflected from a surface.

The display is used to display the percentage of reflected light from the surface. The detect signal is received by the display driver circuit and display, which produces an alpha-numerical representation of the light reflected from the surface.

In the preferred embodiment, the surface is held against the window of the chamber by an absorbing receiver. Light that is transmitted through the surface enters the receiver or chamber to limit outside light and is absorbed. A resilient foam seal having an annular shape is disposed on the receiver to engage the surface. The foam seal absorbs light and helps prevent stray light from entering the chamber.

Other objects and advantages of the invention will be apparent from the following description of a preferred embodiment, the accompanying drawings and the appended claims.

BRIEF DESCRIPTION OF THE DRAWINGS

FIG. 3 is a schematic block diagram of the reflection meter.

DETAILED DESCRIPTION OF THE PREFERRED EMBODIMENT

Figure 1:
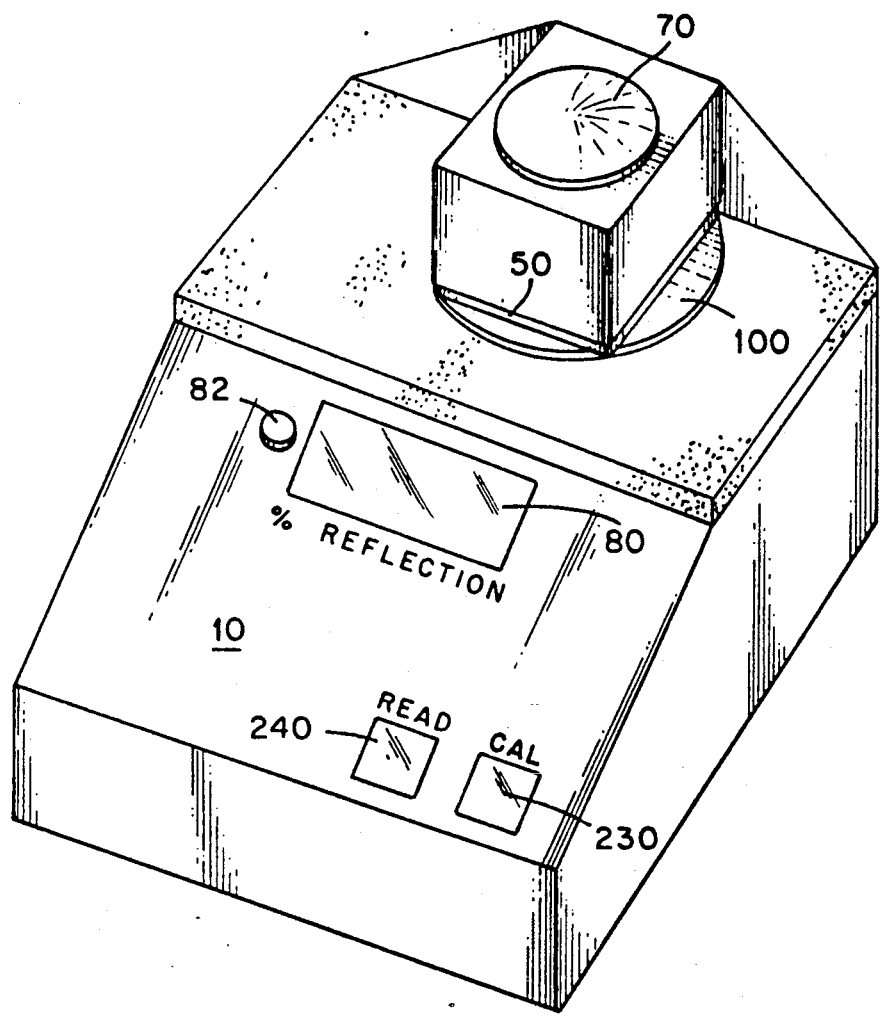
FIG. 1 is a perspective view of the reflection meter with a lens positioned in the meter.

With initial reference to FIG. 1 there is shown the reflection meter 10 with a lens 100 located under the absorbing receiver 50. A handle 70 is attached to the absorbing receiver 50 to retract the absorbing receiver 50 from the lens 100 for removal of the lens 100 from the reflection meter 10. Although the invention is described for use with spectacle lenses, it may be used to measure reflection from a wide variety of objects.

The display 80 displays the percentage of reflected light reflected from the lens 100. A light emitting diode 82 is used to indicate when a valid reading has been obtained and the calculation of the percentage of light reflected is complete. Furthermore, the light emitting diode 82 is off while a reading is being calculated.

Figure 2:
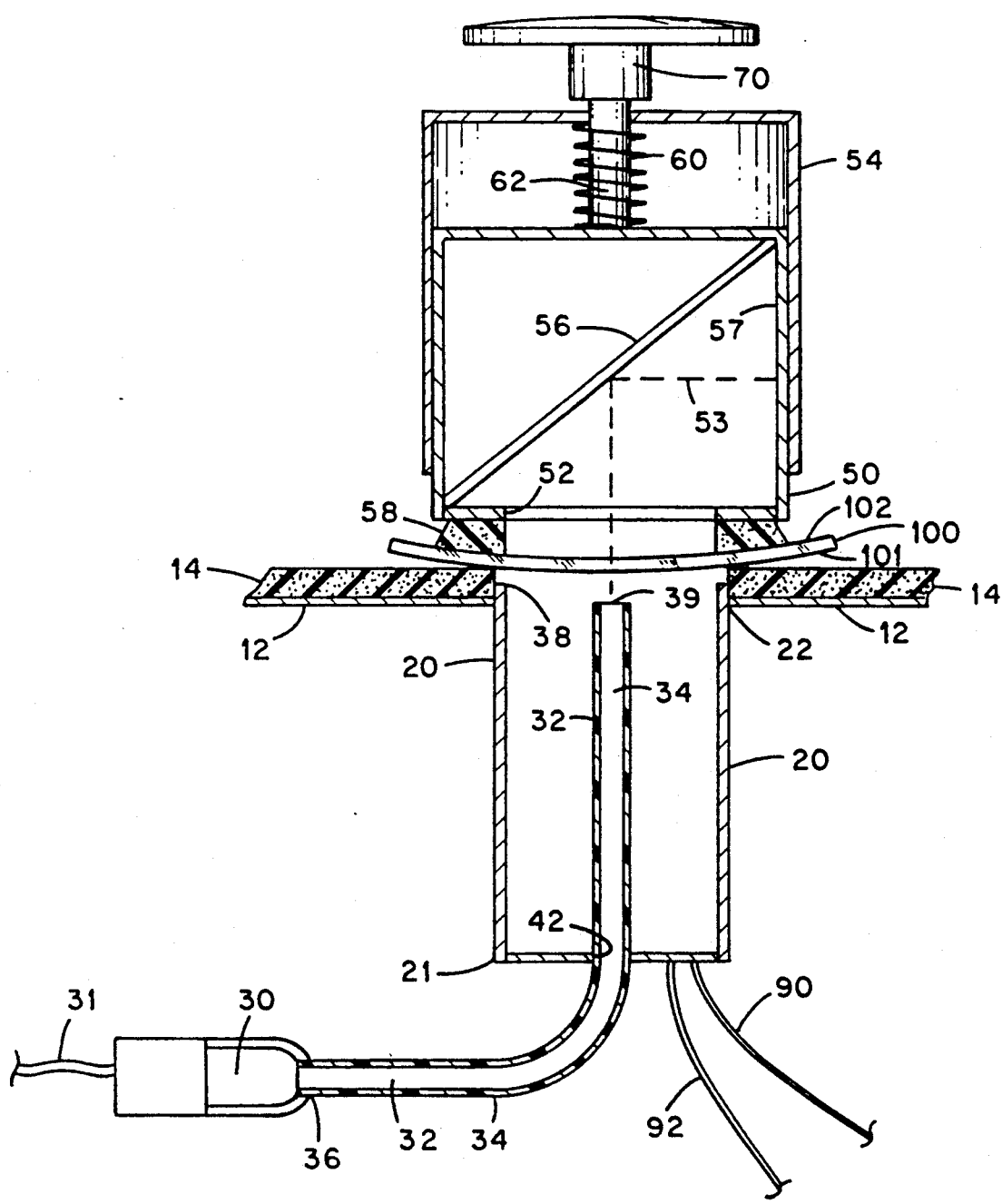
FIG. 2 is an enlarged cross-sectional view of the reflection meter's absorbing receiver and chamber.

Referring to FIG. 2 there is shown a cross-sectional view of the absorbing receiver 50 and the chamber 20 with a lens 100. The light source 30, preferably an incandescent lamp, is located in a covering 32 that isolates the light produced by the light source 30. The covering 32 has an opening to transmit the light from the light source 30 to the lens 100. The light source 30 transmits the light through a fiber optic cable 34. The fiber optic cable 34 carries the light from the first end 36 of the fiber optic cable 34, through the fiber optic cable or the light guide 34 a second end 39.

A chamber 20 having a first end and second ends is attached to the reflection meter's housing 12 at the second end 22 of chamber 20. The chamber 20 is preferably a cylinder having a diameter which is smaller than the lens 100 being measured and larger than the diameter of the fiber optic cable 34 and covering 32. The interior surface of the chamber 20 preferably is highly reflective and reflects any light which strikes the interior surface. A resilient foam 14 surrounds the chamber's 20 second opening 22 and extends higher than the chamber 20 with respect to the reflection meter's housing 12. The resilient foam 14 prevents the lens 100 from becoming scarred or scratched by the chamber 20 or the meter's housing 12.

A photoelectric detector 40, having a diameter equal to the diameter of the chamber 20, is attached to the chamber's first end 21. A hole 42, having a diameter greater than the diameter of the fiber optic cable 34 and covering 32 is preferably located in about the center of the photoelectric detector 40. The fiber optic cable 34 and the covering 32 are positioned through the hole 42 of the photoelectric detector 40.

The light from the light source 30 which is carried through the fiber optic cable 34 is transmitted out the second end 39 of the fiber optic cable 34 striking the lens 100. The light reflects off the lens 100 and the chamber's 20 interior surface and is absorbed by the photoelectric detector 40. The photoelectric detector 40 produces a detect signal on lines 90 and 92 which represents the intensity of the light reflected from the lens 100. The lens 100 has a front surface 101 and a rear surface 102, and light is reflected from the front surface 101, the rear surface 102 and any perturbations inside the lens 100.

In FIG. 2 there is also shown the absorbing receiver 50 preferably in a general shape of a box, having interior and exterior walls. The absorbing receiver 50 has an opening 52 with a diameter smaller than the diameter of the lens 100. The absorbing receiver's opening 52 is positioned adjacent to the chamber 20 and the lens 100. The opening 52 is positioned to receive the light in the general path 51 which is transmitted through the lens 100. Resilient foam 58 is attached to the absorbing receiver 50. The resilient foam 58 has an opening equal to the opening 52 of the absorbing receiver 50 and surrounds the circumference of the absorbing receiver's opening 52.

The absorbing receiver 50 is slidably positioned in the guide frame 54. The guide frame 54 guides the absorbing receiver 50 directly against the lens 100 and holds the lens 100 against the resilient foam 14 and chamber 20. This creates a seal which helps prevent any exterior light from entering into the chamber 20. The absorbing receiver 50 has two positions in the guide frame 54, an open position and a closed position. A handle 70 with rod 62 is attached to the absorbing receiver 50. The handle 70 allows the absorbing receiver 50 to be pulled away from the lens 100, in the open position, to remove the lens 100 from the reflection meter. A spring 62 forces the absorbing receiver 50 against the lens 100 and the chamber 20 in the closed position, when the handle 70 is released.

Inside the absorbing receiver 50 is an absorption plate 56, positioned in the path 51 of the light which enters opening 52. The absorption plate 56 absorbs most of the light striking it and reflects the remainder of the light in the general path 51 to path 53. The light diverted to path 53 is absorbed by the light absorbing interior walls 57 of the absorbing receiver 50.

Referring now to FIG. 3 there is shown a block diagram of the circuitry of the reflection meter 10. The lamp 30 is attached to the lamp circuit 200 through line 31. The lamp circuit 200 is attached to the microprocessor 250 through line 202. The photoelectric detector circuit 220 is coupled to the microprocessor 250 through line 222. The detect signal on lines 90 and 92 is sent into the photoelectric detector circuit 220.

The calibration switch 230 is attached to the microprocessor 250 through line 232. The calibration switch 230 is used to calibrate the reflection meter 10 by placing a reference lens 100, which has a facing surface 101 that reflects 4 percent (4%) of light and a back surface 102 that absorbs the transmitted light, into the reflection meter 10 and then pressing the calibration switch 230. This reference lens is shaped like the lens to be measured i.e., curved or flat. The calibration switch 230 sends a signal on line 232 to the microprocessor 250 to calibrate. The microprocessor 250 then sends a signal to the lamp circuit 200 to turn lamp 30 on. The photoelectric detector 40 senses the amount of light reflected off the reference surface and produces a detect signal on line 31. The detect signal on line 31 is fed into the photoelectric circuit 220 which produces a processed calibrate signal on line 222 representative of the intensity of the light reflected. The microprocessor 250 then receives the processed calibrate signal on line 222 and calibrates itself. The value of the processed calibrate signal is stored and is assumed to constitute a four (4%) percent reflection. All future signals are compared to the stored value of the processed calibrate signal. When calibration is complete, microprocessor 250 sends a display signal to the display circuit 260 to indicate that the reflection meter 10 is calibrated.

The read switch 240 is attached to the microprocessor through line 242. A lens' reflectivity is measured by placing the lens 100 in the reflection meter 10. The read switch 240 is then pressed sending a signal through line 242 to the microprocessor 250. The microprocessor 250 responds by sending a signal to lamp circuit 200, on line 202, to illuminate the lamp 30. The photoelectric detector 40 senses the light reflected from the surface of the lens 100 and sends a detect signal on lines 90 and 92. The photoelectric circuit 40 then produces a processed signal representative of the intensity of the reflected light and transmits it on line 222 to the microprocessor 250.

The microprocessor 250 receives the processed signal on line 222, compares the processed signal to the processed calibrate signal, and calculates a display signal which represents the percentage of light reflected from the surface of the lens 100. The microprocessor 250 produces the display signal and transmits it to the display circuit 260, on line 262. The display circuit 260 receives the display signal and produces a display drive signal on line 264. The display 270 displays a alphanumerical display representative of the display drive signal which is a percentage of the light that was reflect from the surface.

While the form of apparatus herein described constitutes a preferred embodiment of this invention, it is to be understood that the invention is not limited to this form of apparatus, and that changes may be made therein without departing from the scope of the invention which is defined in the appended claims. In the preferred embodiment, reflectivity is displayed as a percentage. Since transparency is inversely related to reflectivity for transparent objects, one could measure reflection and then display transparency for transparent objects. This type of display may be preferred in some applications.

We claim:

1. A reflection meter for measuring the reflection of light from a surface comprising;

a chamber;

a light source for producing light inside said chamber and directing the light in a direction toward the surface to produce reflected light from the surface;

a window formed in said chamber for being positioned adjacent to the surface, for transmitting light from the light source to the surface, and for receiving light reflected from the surface;

a detector for detecting the reflected light and producing a detect signal corresponding to the intensity of the light reflected from the surface, said detector being positioned out of the path of the light produced by the light source and being disposed in the path of the light reflected from the surface, said light source extending through said detector; and an apparatus for receiving the detect signal and producing a display signal representative of the detect signal and indicating the intensity of the light received by the photoelectric detector.

2. The reflection meter of claim 1 wherein said light source further comprises;
   a lamp for producing light;
   a light guide having first and second ends, the first end being disposed to receive light from said lamp and transmit the light to the second end, the second end being disposed to direct the light towards the surface and away from the detector.

3. The reflection meter of claim 1 wherein said light source further comprises:
   a lamp for producing light;
   a fiber optic cable or any other light guide having a diameter and first and second ends, the first end being disposed to receive light from said lamp and transmitting the light to the second end, the second end being disposed to direct light towards the surface and away from the detector;
   said detector including a hole with a diameter greater than the diameter of the fiber optic cable; and
   said fiber optic cable disposed through the hole in said detector.

4. The reflection meter of claim 1 further comprising;
   a light source comprising:
   a lamp for producing light;
   a fiber optic cable or any other light guide having a diameter and first and second ends, the first end being disposed to receive light from said lamp and transmitting the light to the second end, the second end being disposed to direct light towards the surface and away off the detector;
   a chamber having a first and second open ends having diameters greater than the diameter of the fiber optic cable or any other light guide;
   said detector having a diameter equal to the diameter of the first open end of said chamber and having a hole with a diameter greater than the diameter of the fiber optic cable, or any other light guide said detector disposed at the first open end of said chamber for receiving the reflected light from the surface, and closing the first open end of the chamber; and
   said fiber optic cable or any other light guide being disposed through the hole in said detector and extending up to and even with the second open end of the chamber.

5. The reflection meter of claim 1 further comprising an absorbing receiver disposed adjacent to and outside of the chamber and in the path of the light produced by the light source, said absorbing receiver receiving the light from the light source that is transmitted through the surface, and absorbing the transmitted light.

6. The reflection meter of claim 1 further comprising an absorbing receiver receiving the light produced by the light source hat transmitted through the surface and having an opening smaller than the diameter of the surface for receiving the transmitted light, said absorbing receiver disposed adjacent to and outside said chamber and in the path of the light produced by the light source;
   an absorbing plate disposed in said absorbing receiver and in the path of the light from the light source for absorbing the light from the light source that is transmitted through the surface into said absorbing receiver, said absorbing plate diverting light into said absorbing receiver.

7. The reflection meter of claim 1 further comprising:
   means for positioning the surface adjacent said window of said chamber.

8. The reflection meter of claim 1 further comprising;
   means for positioning the surface adjacent said window of said chamber comprising;
   an absorbing receiver having an opening with a circumference and a diameter smaller than the diameter of the surface, said absorbing receiver disposed adjacent to and outside said chamber and in the path of the light produced by the light source said absorbing receiver opening being positioned for receiving the light produced by the light source that is transmitted through the surface;
   an absorbing plate disposed in said absorbing receiver and in the path of the light from the light source for absorbing the light from the light source that is transmitted through the surface into said absorbing receiver;
   resilient foam having an opening with a diameter equal to the opening of the absorbing receiver and disposed and covering the circumference of the opening of the absorbing receiver;
   a guide frame for positioning the absorbing receiver opening against the surface, said absorbing receiver being slidably positioned in said guide frame for locating the opening of said absorbing receiver and said resilient foam against the surface and positioning the surface against said window of said chamber preventing any exterior light from hitting the photoelectric detector; and
   a handle attached to the absorbing receiver for releasing the absorbing receiver from the surface.

9. The reflection meter of claim 1 further comprising:
   light controlling means for controlling the intensity of the light source;
   detector circuit for producing the detect signal from the detector;
   display controlling means for controlling the display of the percentage of light reflected from the surface; and
   a microprocessing means for coordinating the operation of the light controlling means, the detector circuit and the display controlling means.

10. The reflection meter of claim 1 further comprising;
    a light circuit for controlling the intensity of the lighting from said light source;

a circuit for receiving the detect signal from a photoelectric cell and producing a processed detect signal corresponding to the intensity of the light reflected from the surface;

a microprocessor for controlling said light circuit and said photoelectric circuit and for receiving the processed detect signal and calculating the percentage of light from the light source reflected from the surface and producing a display signal;

a display circuit for receiving the display signal and displaying the percentage of reflected light from the surface.

11. The reflection meter of claim 1 further comprising:

a reference surface;

means for measuring of reflection off reference surface and producing a processed calibrate signal;

a light circuit for controlling the intensity of the lighting from said light source;

a detector circuit for receiving the detect signal from the cell and producing a processed detect signal corresponding to the intensity of the light reflected from the surface;

a microprocessor for controlling said light circuit and said detector circuit and for receiving the processed calibrate signal from said measuring means and calibrating said microprocessor to the reflected light from the reference surface and for receiving the processed detect signal from said detector circuit and calculating the percentage of light from the light source reflected from the surface and producing a display signal representative of the percentage of the light reflected from the surface;

a display circuit for receiving the display signal and producing display drive signals; and a display for receiving the display drive signals and displaying the percentage of light reflected from the surface in alpha-numeric characters.

12. The reflection meter of claim 1 further comprising:

a reference lens having a light reflecting front surface, which has a configuration like the surfaces to be tested by the meter, and a light absorbing rear surface, said reference lens for being positioned adjacent to the window to reflect light from the light source off of the front surface;

calibration switch means for producing an initiation signal in response to actuation;

said apparatus comprising processing means responsive to the initiation signal to cause the light source to illuminate the reference lens, to receive a detect signal corresponding to the intensity of light reflected from the front surface, and to store a calibrate value corresponding to the detect signal for comparison to future detect signals; and said processing means being operable to compare detect signals to said calibrate value and produce an intensity signal based on such comparison.

* * * * *